United States Patent [19]

Tisch

[11] 4,235,098
[45] Nov. 25, 1980

[54] AIR SAMPLING APPARATUS

[76] Inventor: Wilbur P. Tisch, 8368 Bridgetown Rd., Village of Cleves, Ohio 45002

[21] Appl. No.: 62,928

[22] Filed: Aug. 2, 1979

[51] Int. Cl.$^3$ .............................................. G01N 1/24
[52] U.S. Cl. ................................. 73/28; 73/421.5 R; 55/270; 55/271
[58] Field of Search ............. 55/212, 270, 271, 385 F, 55/472; 73/28, 421.5 R

[56] References Cited

U.S. PATENT DOCUMENTS

| | | | |
|---|---|---|---|
| 3,104,542 | 9/1963 | Scoggins | 73/28 |
| 4,151,742 | 5/1979 | Howlett | 73/28 |

FOREIGN PATENT DOCUMENTS 612156  4/1976  U.S.S.R. ............................. 73/421.5 R

OTHER PUBLICATIONS

High Volume Air Samplers, General Metal Works, Inc., Models; GMWL-2000, GMWL-2000H, GMWR-5000, GMWS-2310 Accu-Vol TM, GMWT 2200, & Accessories, 8368 Bridgetown Road, Cleves, Ohio 45002, pp. 3-11, Bulletin No. GMW-75, SM-W-P-975.

*Primary Examiner*—David L. Lacey
*Attorney, Agent, or Firm*—Wood, Herron & Evans

[57] ABSTRACT

Air sampling apparatus having a housing covered by a roof which creates a passageway between the housing and the roof. The housing has an open upper end and a plate with a hole through it for mounting a filter and a blower by which air is drawn through the filter. A cover plate for the filter is provided with means for removing the plate when air is to be drawn through the filter and replacing the plate over the filter when the air blower is inoperative.

6 Claims, 6 Drawing Figures

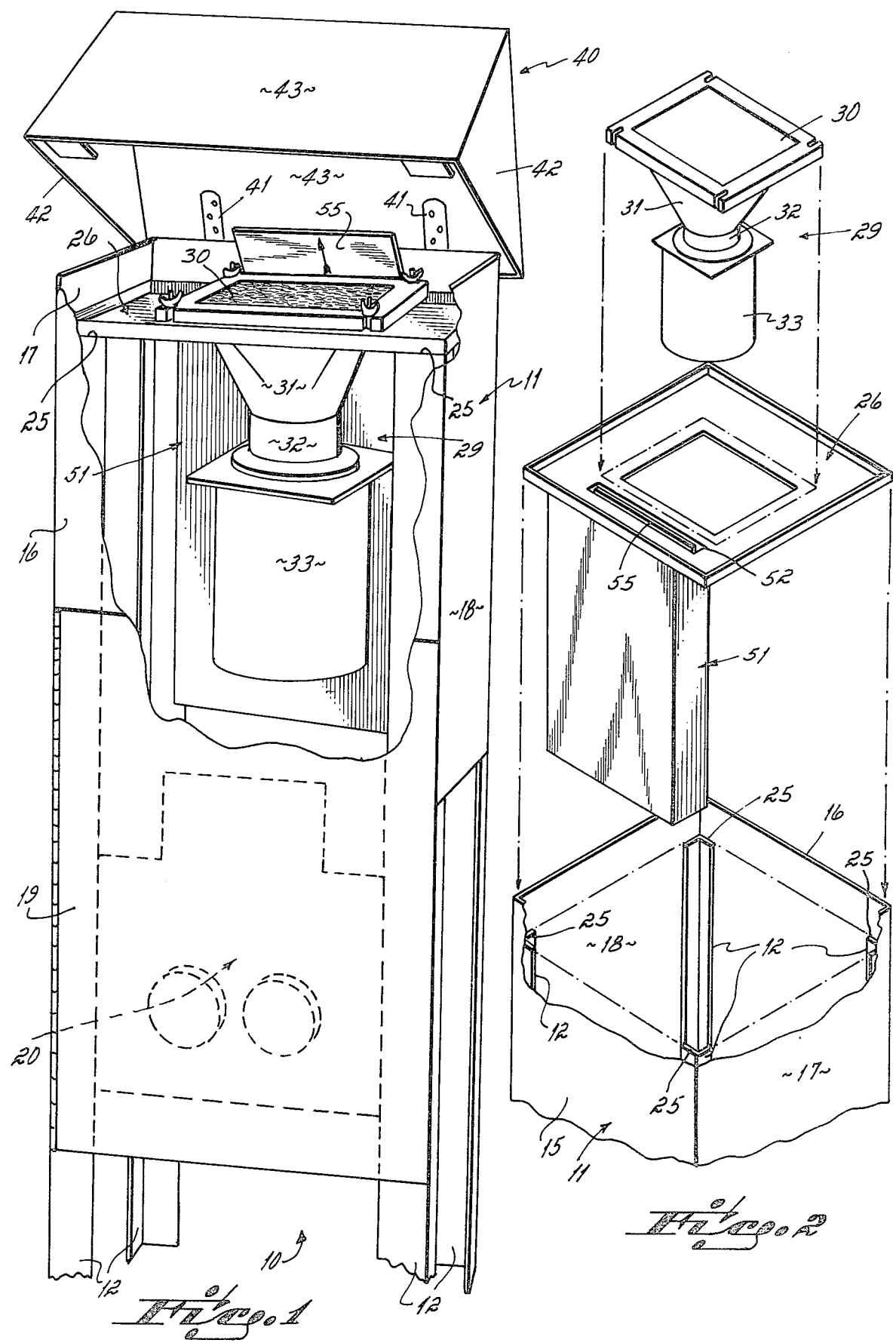

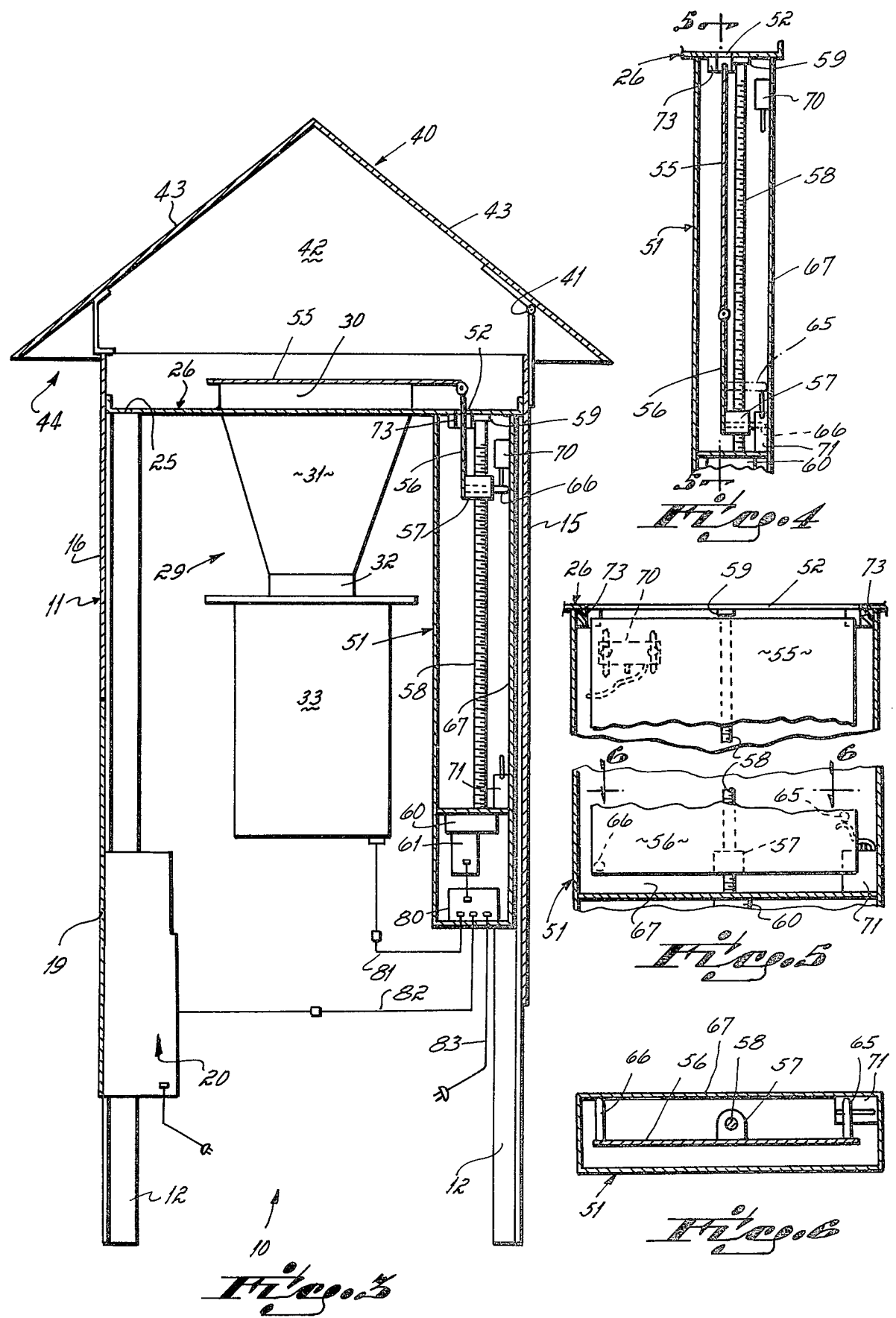

AIR SAMPLING APPARATUS

This invention relates to an air sampling apparatus, and more particularly, to air sampling apparatus wherein a mechanism is provided to protect the filter onto which particulate material in the air is collected.

Environmental protection requires sampling of the air around industrial concerns and other areas where particulate material which contaminates the air quality is generated. The sampling system should be accurate enough in order to provide evidence which would be useful in forcing compliance with air quality standards passed into law by Federal, state and local governments.

There are presently air sampling mechanisms on the market which are used by Federal, state and local governments as well as industrial concerns to take regular samples of the particulate material in the air at various locations in a political subdivision such as a city or county in the United States. These mechanisms are built to standard specifications as published in *Federal Register*, Volume 36, No. 84, Apr. 30, 1971. In general, the mechanisms include a housing, an open upper end, an aperture plate at the upper end of the housing having a hole therethrough, a filter mounted over the hole and a blower and motor combination which draws air through the filter. A timer is provided to start and stop the blower. A gable roof overhangs the housing all around its perimeter thereby creating an air passageway of approximately 90 square inches through which the air in the atmosphere is drawn into the housing through the filter.

The sample taking procedure involves the first weighing of the filter, placing it in the air sampling mechanism, drawing air through the filter for a period of twenty-four hours and thereafter weighing the filter. The increase in weight of the filter provides the measure of particulate material in the surrounding air during the test period.

A normal practice for taking samples involves the operation of the device every sixth day, although this obviously can be varied and, in fact, is varied in accordance with the number of samples the sampling organization wishes to take over a given period. Some units are used to take a sample every day.

Following the normal practice, however, and by way of example, a city sampling crew would weigh a group of filters and spend the day driving around the city to the various sampler locations to place the filters in the units. At the time set on the timer, the unit would be caused to operate for the requisite twenty-four hour period, after which the unit would shut down. Sometime later, the crew would pick up the now used filters and weigh them to make the determination of the particulate material in the air during the test period. At the time of picking up the used filters, the new filters would be inserted in the machines so that only one trip would be required for each sample taken.

It can be seen that with this routine all of the time that the sampler is not operating the filter will be collecting fugitive dust, that is, particulate material which is blown into the sampling unit by the wind around the unit. The amount of particulate material which is weighed will be in error by the amount of fugitive dust which was collected during the time the unit was not in use.

It has been an objective of the present invention to provide sampling apparatus which eliminates the exposure of the filter to fugitive dust during quiescent or non-operating periods of the sampling unit. This objective is attained by providing a filter cover and a mechanism for applying the filter cover to the filter at all times when the unit is not actually being run to take a sample.

The implementation of the concept of providing a filter cover has created additional problems, namely, how to remove a filter cover and where to store it so that it will not block any portion of the 90 square inches passageway through which air is brought into the sampling unit. For example, a filter cover cannot be simply raised up into the gable part of the roof, for that would alter the configuration of the gable and cause the unit to be at variance with the prescribed specifications.

It has been proposed to lower the gable roof onto the main housing to close the passageway between the main housing and the roof, thus protecting the filter. Among other things, this proposal involves a complex, expensive mechanism not suitable for retrofitting.

These problems have been solved by the present invention by providing a plate movable vertically along the inside of the housing and hinging a filter cover plate to the vertically-movable plate. A mechanism, in the preferred embodiment a screw, is provided to raise and lower the vertically-movable plate so that in its upper position the filter cover is caused to fall horizontally on the filter, and in its lower position the filter cover is caused to swing to a vertical plane inside the housing of the sampling unit.

Another objective of the invention has been to provide a filter cover which can be very easily added to existing air sampling apparatus. This objective is achieved primarily by creating an inverted L-shaped unit formed by a horizontal aperture plate which removably supports a filter-blower assembly, and a vertical housing depending from one edge of said aperture plate, the housing containing a mechanism for operating the filter cover plate. This unit can be installed in existing apparatus by removing the existing aperture plate and substituting the L-shaped unit for it.

The several features and objectives of the invention will become more readily apparent from the following detailed description taken in conjunction with the accompanying drawings in which:

FIG. 1 is a partially broken away perspective view of the invention;

FIG. 2 is a fragmentary disassembled perspective view;

FIG. 3 is a cross-sectional view through the apparatus with the cover plate in place on the filter;

FIG. 4 is a fragmentary view of a portion of FIG. 3 with the cover plate removed from the filter;

FIG. 5 is a cross-sectional view taken on line 5—5 of FIG. 4; and

FIG. 6 is a cross-sectional view taken on line 6—6 of FIG. 5.

The apparatus of the invention is illustrated at 10 and includes a housing 11 supported on four angle legs 12 which extend almost to the top of the housing 11. The housing has a rear wall 15, a front wall 16 and side walls 17 and 18. The front wall is partly formed as an access door 19. A timer 20 is supported in the lower portion of the housing and is accessible through the door 19.

The upper end 25 of the angle legs 12 provides a four-point horizontal support for an aperture plate 26. The aperture plate has a rectangular hole or aperture about 7 inches by 8½ inches. A filter and blower assembly 29 consisting of a filter receptacle 30, a funnel 31, a blower 32 and a blower motor 33 are supported on the aperture plate 26. The assembly 29 is made as a unit and is mounted on the plate simply by vertically inserting the blower motor through the aperture 27 until the filter receptacle 30 which is larger than the hole rests upon the aperture plate. The filter receptacle is adapted to receive and retain a filter or preferably a filter cartridge.

A gable roof 40 is mounted by hinges 41 to the back wall 15. The gable roof has triangular end walls 42 and two inclined roof panels 43. At the lower ends, the end walls and inclined roof panels define a rectangle which is substantially larger in horizontal dimension than the housing 11. The thus created overhang between the roof and the housing, all around the perimeter of the housing, creates a rectangular passageway 44 (FIG. 3) of approximately 90 square inches through which air from the atmosphere can flow into the space above the filter receptacle and thereafter be drawn through the filter in the receptacle by the blower and motor.

The mechanism thus far described (except for the new modifications to the plate 26 which will be described) has been used for many years. The invention which is mounted in the sampler is best shown in FIGS. 1, 2 and 3.

The invention is an inverted L-shaped unit having the horizontal aperture plate 26 at its upper end, a vertical housing 51 attached to the horizontal aperture plate and depending from it. The aperture plate 26 is substantially identical to the aperture plates previously employed except for the slight modifications required to support the housing 51 and filter cover. The aperture plate 26 contains a slot 52 through which a filter cover will pass as it moves between covered and uncovered positions. A filter cover 55 is hinged to a vertical nut plate 56 which carries a threaded nut 57. The nut plate 56 is supported on a screw 58 whose upper end is journalled in a bearing 59 and whose lower end is mounted in a gear box 60. A reversible capacitor motor 61 is mounted on the gear box and is connected through the gears in the gear box to drive the screw in one direction to draw the nut 57 and nut plate 56 downwardly and in the opposite direction to raise the nut 57 and nut plate 56.

As best seen in FIG. 6, the nut plate has two Nylon posts 65, 66, one on each side, which ride on a back wall 67 of the cover housing 51 to resist twisting of the nut plate and to maintain it in a plane parallel to the back wall 67. One post 66 cooperates with a limit switch 70 mounted on the upper portion of the back wall 67. The other post 65 is engageable with a lower limit switch 71 mounted on the lower portion of the back wall. A pair of Nylon guides 73 are mounted adjacent the slot 52 to guide the cover plate 55 as it slides into the housing.

The unit includes a control circuit 80 from which three electrical connectors 81, 82 and 83 project. The control unit 80 interconnects the blower motor 33, capacitor motor 61, timer 20 and the limit switches 70 and 71 to effect removal of the cover plate 55 when the unit is energized and to return the cover plate 55 to its protecting position when the unit is de-energized.

The unit is adapted to replace the existing aperture plate of the sampling unit previously described and in replacing that aperture plate, providing for a filter cover plate and controls and operating mechanism therefor.

The retrofitting of existing units is performed very simply. The existing filter plate is removed and after the blower and filter assembly is removed, the aperture plate is discarded. The blower and filter assembly is then inserted in the new aperture plate 26 (as seen in FIG. 2) and the new aperture plate is positioned in the main housing 11 with the cover plate housing 51 being disposed parallel and adjacent to the back wall 15. One of the conductors 83 is connectable to a 120 volt power supply, another conductor 81 is connected to the blower motor, and the third conductor 82 is connected to the timer 20 in the same way that the blower was previously connected to the timer. Thus, the control circuit 80 is simply inserted between the blower and the previously existing timer.

The timer which had previously been connected to the 120 volts could optionally be connected to another 120 volts supply or, alternatively, could be connected to an outlet in the control circuit 80 which is directly connected to the conductor 83 which is in turn connected to the 120 volt supply.

The limit switch 70 at the upper portion of the housing is a single pole, double throw switch. The limit switch 71 at the lower portion of the housing is a double pole, double throw switch. The circuit elements, limit switches, motors and timer are interconnected through the control circuit 80 which includes a pair of capacitors for the reversible capacitor motor 61 and a double pole, double throw relay to provide the following sequence of operations:

Let it be assumed that a filter is in place in the receptacle 30 and is covered by the cover plate 55, the nut plate 56 being at the upper end of the screw 58. When the time set in the timer arrives, the motor 61 is energized and rotates in a direction to cause the nut plate 56 to descend. As the nut plate descends, the cover plate 55 passes through the slot 52 and in passing over the edge of the slot in the aperture plate 26, is cammed to a vertical orientation. The blower motor 33 is prevented from starting at this stage. When the nut plate completes its descent on the screw 58, the post 65 engages limit switch 71 which, through the relay in the control circuit, de-energizes the motor 61 and energizes the blower motor 33. The blower motor continues to operate for a period of twenty-four hours (or any other period set on the timer). At the conclusion of the selected period, the blower motor is de-energized and the reversible motor 61 is energized to cause the screw to rotate in the opposite direction. The screw continues to rotate causing the nut plate 56 to rise. As the nut plate rises, the cover plate 55 projects through the slot and will normally flop over onto the filter receptacle covering it and protecting it against fugitive dust. If for some reason the cover plate does not flop over naturally, it will engage the inclined roof panel 43 which will cam it past vertical whereupon gravity will flop the cover plate onto the filter receptacle. At the top of the screw, the post 66 will engage the limit switch 70 and de-energize the motor 61. The unit will then stay in that de-energized condition until the sample is removed and a new one substituted. The removed sample can then be weighed with the certain knowledge that no fugitive dust has affected the weight of the particulate material accumulated during the preselected timer period. Further, a new filter can be placed in the apparatus with the certain knowledge that it will remain covered against the incidence of fugitive dust until the beginning of the predetermined timer period.

Having described my invention, I claim:
1. In air sampling apparatus having,
    a housing, a roof fixed over said housing and spaced above said housing to permit air to flow into said housing between said roof and said housing, a filter located below said roof, means for drawing air through said filter, a cover plate, means mounting said cover plate with respect to said filter for movement into and out of positions covering said filter, and means for moving said cover plate to a covering position when no air is to be drawn through said filter and uncovered position when air is to be drawn through said filter.

2. In air sampling apparatus comprising, a rectangular housing open at its upper end, a roof hinged to said one side of said housing and adapted to cover said upper end while permitting air to flow into said housing between the upper end and said roof, a support plate mounted in said upper end and having an opening therethrough, a filter receptacle in said opening, a filter in said receptacle, a blower and motor mounted below said filter to draw air through said filter, the improvement comprising, a cover plate movable between a first position overlying said filter receptacle and a second position lying vertically along one side of said housing, and means including a control circuit for moving said cover plate to said first position when said blower motor is inoperative and said second position when said blower motor is operating.

3. Air sampling apparatus as in claim 2 in which said moving means comprises, a vertical screw, reversible means for rotating said screw, a nut and nut plate threaded onto said screw for vertical movement when said screw rotates, said cover plate hinged to said nut plate to swing to said first position when said nut plate rises to the upper portion of said screw and to said second position when said nut plate is lowered to the lower portion of said screw.

4. Air sampling apparatus as in claim 3, said roof being gabled and presenting an inclined surface immediately above said cover plate in its second position and engageable by said cover plate as it moves from said second position to said first position whereby said inclined surface is adapted to cam said cover plate from a vertical plane in said second position to a horizontal plane in said first position.

5. Air sampling apparatus as in claim 3 further comprising a pair of posts mounted on said nut plate and engageable with the walls of said rectangular housing to resist twisting of said nut plate.

6. Air sampling apparatus comprising, a main housing having an open upper end, a roof fixed over said housing and spaced above said housing to permit air to flow into said housing between the roof and said housing, a horizontal support at the upper end of said housing below said roof, a horizontal aperture plate resting on said support and having a central hole therethrough, a filter and blower assembly mounted on said aperture plate, a vertical control housing mounted on said aperture plate and depending therefrom into said main housing, a filter cover positioned adjacent to said control housing, filter cover moving means in said control housing and connected to said cover, control means in said housing connected to said filter cover for moving said filter cover moving means between a position covering said filter and a position uncovering said filter.

* * * * *